United States Patent [19]

Morrison

[11] 3,978,862

[45] Sept. 7, 1976

[54] SURGICAL CUTTING DEVICE

[75] Inventor: Marshal Morrison, Comstock, Kalamazoo, Mich.

[73] Assignee: Stryker Corporation, Comstock Township, Kalamazoo County, Mich.

[22] Filed: Aug. 26, 1974

[21] Appl. No.: 500,373

[52] U.S. Cl. .................................. 128/317; 30/393
[51] Int. Cl.² ................... A61B 17/14; B27B 19/04
[58] Field of Search ..................... 30/392, 393, 394; 128/317

[56] References Cited
UNITED STATES PATENTS

| | | | |
|---|---|---|---|
| 1,481,055 | 1/1924 | Fullbright | 30/392 X |
| 2,239,681 | 4/1941 | Marshall | 30/393 |
| 2,630,148 | 3/1953 | Ferguson | 30/393 |
| 2,705,980 | 4/1955 | Papworth | 30/393 |
| 2,793,661 | 5/1957 | Olson | 30/393 |
| 2,946,358 | 7/1960 | Bruck | 30/393 |
| 2,961,016 | 11/1960 | Papworth | 30/393 |
| 3,905,105 | 9/1975 | Tuke | 128/317 X |

Primary Examiner—Channing L. Pace
Attorney, Agent, or Firm—Woodhams, Blanchard and Flynn

[57] ABSTRACT

A surgical cutting device, particularly a sagittal saw, having an elongated tubular housing containing therein a driving mechamism which extends outwardly from one end of the housing and has a saw blade mounted thereon. A driving connection, such as a flexible drive cable or the like, extends into the other end of the housing and is drivingly connected to the driving mechanism. The driving mechanism includes a crank structure connected between a rotatable input shaft and one end of a blade mounting member, which member has the saw blade mounted on the other end thereof. A pivot structure coacts with the blade holding member for permitting angular oscillation of the blade holding member while also simultaneously permitting the blade holding member to be reciprocated in the longitudinal direction thereof. The crank structure causes the blade holding member to be simultaneously angularly oscillated and linearly reciprocated, whereby the blade is cyclically moved around a substantially elliptical path.

10 Claims, 10 Drawing Figures

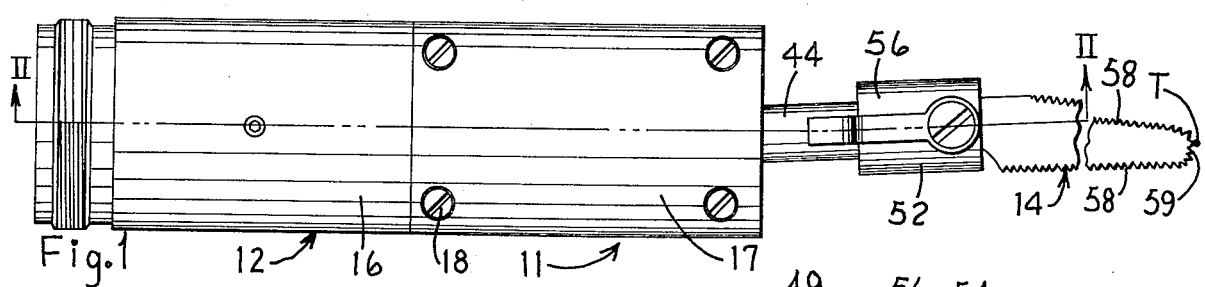
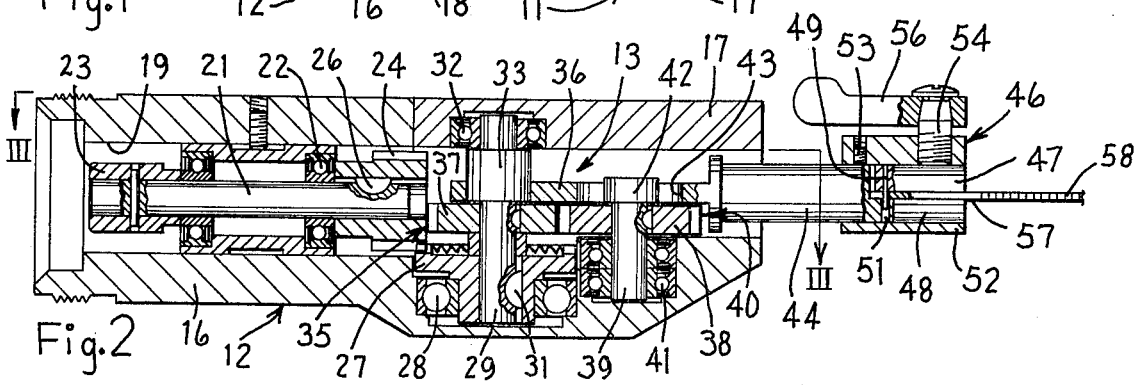
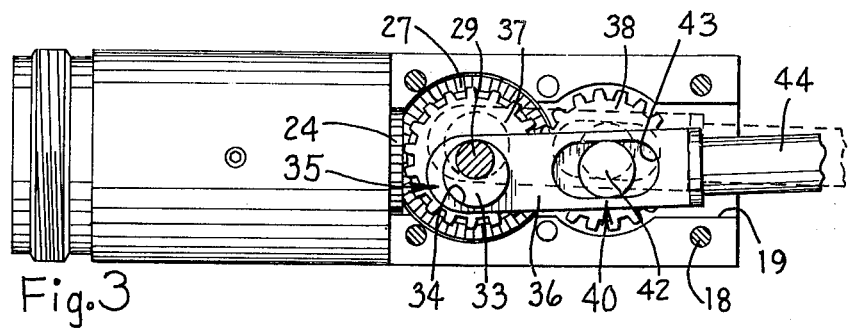
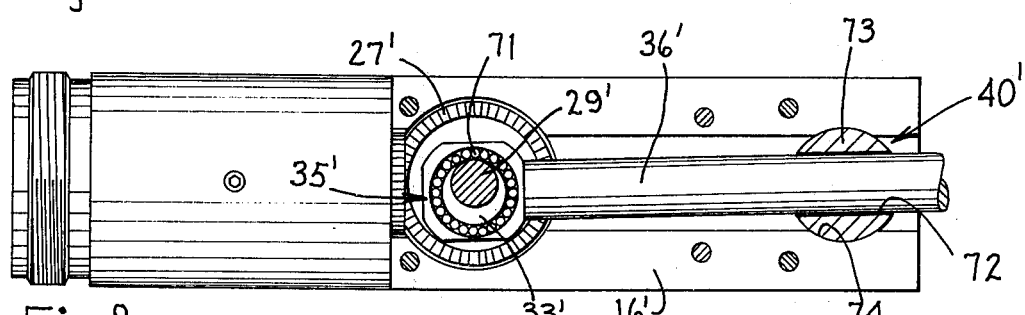
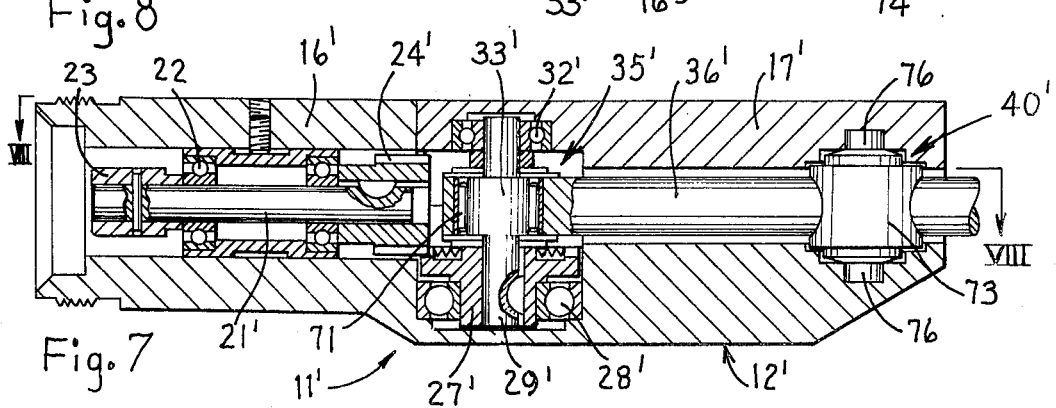

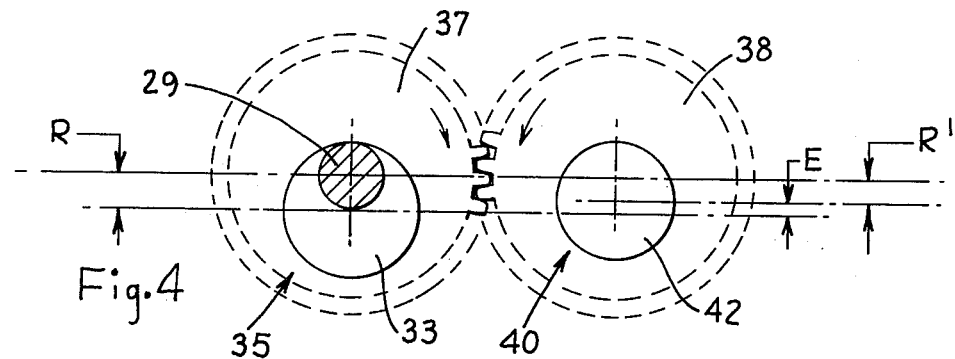
Fig.4
Fig.5
Fig.6
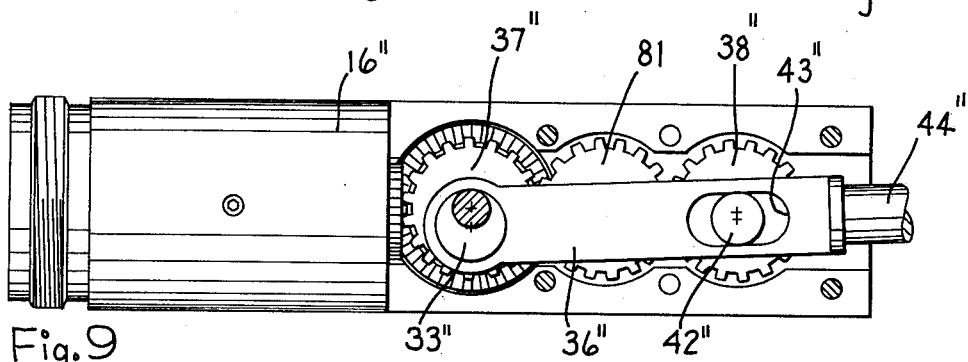
Fig.9
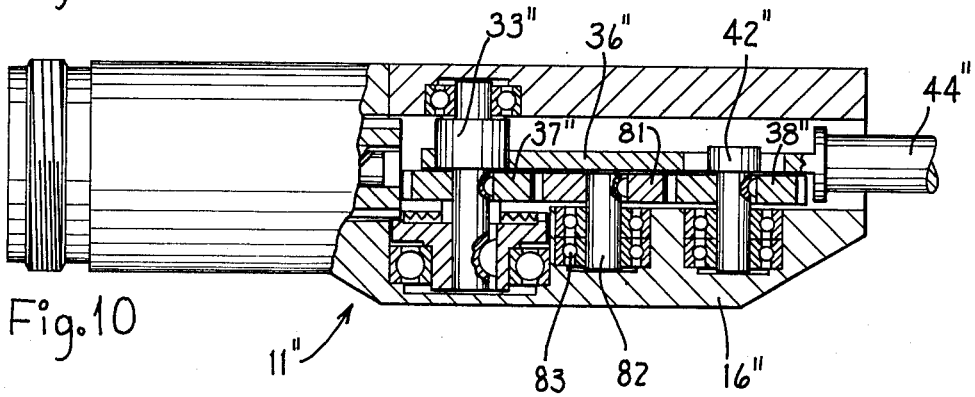
Fig.10

SURGICAL CUTTING DEVICE

FIELD OF THE INVENTION

This invention relates to an improved surgical cutting device of the type commonly referred to as a sagittal saw.

BACKGROUND OF THE INVENTION

Surgical saws of the sagittal type for performing bone surgery have been extensively utilized for many years. These saws have normally employed an elongated saw blade having an arcuate toothed segment on one end thereof, with the other end of the blade being pivotally mounted to permit angular oscillation of the blade. Typical such saws are disclosed in U.S. Pat. Nos. 2,854,981 and 3,678,934, which saws have been satisfactorily usable for forming short longitudinal cuts within a bone. These saws, however, have not permitted the blade to be moved laterally along the bone to permit formation of a long cut without endangering the bone or the surrounding tissue. These saws have also not been satisfactory for use with deep cuts since deep cuts require that the toothed edge of the blade be spaced a greater distance from the pivot axis, thereby resulting in larger peripheral movement which often is of sufficient magnitude as to damage the tissue surrounding the bone.

Accordingly, it is an object of the present invention to provide an improved surgical device, particularly a sagittal saw, which overcomes the above-mentioned disadvantages. Particularly, it is an object of the present invention to provide an improved surgical saw which can enter the side of a bone and can then be moved laterally as to permit the formation of a long lateral cut without endangering the bone or the surrounding tissue. It is also an object of the present invention to provide a surgical saw which can be utilized for rather deep cuts while maintaining the cutting stroke of the saw rather small, such as less than approximately one-eighth inch, in order to avoid damage to the surrounding tissue.

In the present invention, the desired lateral movement of the cutting edge is achieved by moving the cutting edge of the saw along a substantially endless path, which path is formed as a closed loop and has a portion thereof defining the cutting stroke of the saw.

Other objects and purposes of the present invention will be apparent to persons acquainted with devices of this type upon reading the following specification and inspecting the accompanying drawings.

BRIEF DESCRIPTION OF THE DRAWINGS

FIG. 1 is a side elevational view of a sagittal plane, surgical saw according to the present invention.

FIG. 2 is a cross-sectional view taken substantially along the line II—II in FIG. 1.

FIG. 3 is a plan view similar to FIG. 1 but illustrating the cover of the handpiece removed, said view being taken substantially along the line III—III in FIG. 2.

FIG. 4 is an enlarged diagrammatic illustration of the driving crank and pivot structure associated with the blade holding member of the embodiment illustrated in FIGS. 1–3.

FIG. 5 illustrates the path of movement of the cutting edge associated with the free end of the blade when utilizing the driving mechanism possessed by the embodiment of FIGS. 1–4.

FIG. 6 illustrates a modified path of movement as experienced by the cutting edge of a blade when using the modified mechanism illustrated in FIGS. 7 and 8.

FIG. 7 is a cross-sectional view similar to FIG. 2 and illustrating a modification of the present invention.

FIG. 8 is a view taken substantially along line VIII—VIII in FIG. 7.

FIG. 9 is a partial cross-sectional view similar to FIG. 2 and illustrating a further modification of the present invention.

FIG. 10 is a side elevational view of FIG. 9 but with the handpiece cover removed.

Certain terminology will be used in the following description for convenience in reference only and will not be limiting. For example, the words "upwardly," "downwardly," "rightwardly" and "leftwardly" will refer to directions in the drawings to which reference is made. The words "inner" and "outer" will refer to the geometric center of the device and designated parts thereof. The terms "front" and "rear" will have reference to the right and left ends, respectively, of the surgical saw and parts thereof as appearing in FIGS. 1–3 and 7–10. Said terminology will include the words above specifically mentioned, derivatives thereof and words of similar import.

SUMMARY OF THE INVENTION

The sagittal-type surgical saw of the present invention comprises a handpiece having therein a driving mechanism connected to one end of an elongated blade holding member which projects outwardly of the housing and has a cutting blade fixedly mounted thereon. The blade holding member is supported intermediate its ends by a pivot structure which permits angular oscillation of the blade and also permits the blade holding member to be slidably displaced in the longitudinal direction thereof. The driving mechanism includes a crank connected to the blade holding member for causing same to be simultaneously angularly oscillated and linearly reciprocated, whereby the cutting edge of the blade is moved along a closed loop, a portion of which loop constitutes the actual cutting stroke of the saw. In a preferred embodiment, the pivot structure is defined by a rotatably eccentric which rotates in synchronism with the crank whereby the cutting edge of the blade is moved along a closed endless path.

DETAILED DESCRIPTION

FIGS. 1–3 illustrate therein a preferred embodiment of a surgical cutting device 11, particularly a sagittal saw, constructed according to the present invention. The cutting device 11 includes a handpiece 12 having a driving mechanism 13 housed therein. A toothed cutting blade 14 projects outwardly from the forward end of the handpiece 12.

The handpiece 12 comprises an elongated tubular housing 16 having a removable cover 17 associated therewith, which cover is of substantially semicylindrical configuration and is fixed to the housing 16 by a plurality of fastening devices, such as screws 18. The housing 16 has an elongated opening 19 extending therethrough.

An input shaft 21 is disposed within one end of the housing 16 and is rotatably supported thereon by antifriction bearings 22. The input shaft 21 has a drive coupling 23 on the input end thereof, which coupling is adapted to be releasably connected to a conventional drive device, such as a rotatable flexible drive cable associated with an external power source, or a pneumatic or electric motor.

The driving mechanism 13 is disposed within the opening 19 and is driven by the input shaft 21. For this purpose, shaft 21 has a drive gear 24 on the forward end thereof, which gear 24 is nonrotatably connected to the shaft 21, as by a key 26, and is disposed in meshing engagement with a crown gear 27. Gear 27 is rotatably supported on the housing by an antifriction bearing 28 and is nonrotatably coupled to a drive shaft 29 by a key 31. The upper end of shaft 29 is rotatably supported by a further antifriction bearing 32 which is mounted on the cover 17. The rotational axis of the shaft 29 is substantially perpendicular to the rotational axis of the input shaft 21 as illustrated in FIG. 2.

The driving mechanism 13 has a crank structure 35 associated therewith and disposed in driving engagement with the rearward end of an elongated blade holding member 36. The crank structure 35 includes a crank or eccentric 33 fixedly secured to the drive shaft 29 and is rotatably but snugly received within an opening 34 formed adjacent the rearward end of the blade holding member 36.

The blade holding member 36 also has a pivot structure 40 associated therewith for permitting angular oscillation of the blade holding member 36 and of the blade 14 mounted thereon. The pivot structure 40, in a preferred embodiment of the invention, is located intermediate the ends of the blade holding member as illustrated in FIGS. 2 and 3.

The pivot structure 40 includes a rotatable crank or eccentric 42 accommodated within a slot 43 formed in the blade holding member 36, which slot 43 is elongated in the longitudinal direction of the member 36 and has a width substantially equal to or only slightly greater than the diameter of the eccentric 42. The eccentric 42 is fixedly secured to a shaft 39 which is disposed in parallel relationship to the shaft 29 and is supported on the housing 16 by antifriction bearings 41. The shaft 39 is driven from the shaft 29 and for this purpose is provided with a gear 38 nonrotatably secured thereto, which gear is disposed in meshing engagement with a further gear 37 which is nonrotatably mounted on the shaft 29.

The drive eccentric 33 has an eccentricity R (see FIG. 4) relative to the rotational axis of the shaft 29, whereas the pivot eccentric 42 has an eccentricity R' relative to the rotational axis of the shaft 39, which eccentricity R' is less than the eccentricity R by a differential which has been designated E in FIG. 4. The purpose of this differential in eccentricity E will be explained in detail hereinafter.

FIG. 4 also illustrates therein a further desirable feature of the present invention. Particularly, the eccentrics 33 and 42 are both offset in the same direction relative to a plane passing through the axis of the shaft 29 and 39 when the eccentrics are in their positions of maximum eccentricity. That is, both of the eccentrics 33 and 42 are simultaneously in their positions of maximum eccentricity, and both eccentrics are located on the same side of this specified plane when in their positions of maximum eccentricity.

The blade holding member 36 has a cylindrical shank portion 44 formed on the forward end thereof, which portion 44 projects outwardly from the handpiece 12 and has quick release clamping means 46 associated therewith for permitting the blade 14 to be releasably attached to the member 36. The clamping means 46 includes a semicylindrical section 47 which is disposed opposite a semicylindrical projection 48 formed on the end of the shank 44. The cylindrical section 47 can be formed by cutting same from the shank 44. The section 47 has a guide pin 49 fixed thereon and disposed so as to extend into a guide opening 51 formed in the projection 48. A sleeve 52 is fixed to the forward end of the shank 44, as by means of a set screw 53, and is disposed in surrounding relationship to the section 47 and projection 48. The sleeve 52 has a threaded clamping member 54 rotatably supported thereon and positioned to engage the section 47 so as to move same into tight clamping engagement with the projection 48. The clamping member 54 is controlled by a manually movable operating lever 56.

The clamping means 46 is designed to coact with a plate-like shank 57 formed on the rearward end of the blade 14, which shank 57 is adapted to be clampingly engaged between the section 47 and the projection 48 as illustrated in FIG. 2 The shank 57 has a slot (not shown) formed therein and projecting outwardly through the open end thereof, which slot receives therein the pin 49 in a conventional manner.

The blade 14, as illustrated in FIG. 1, is elongated in the longitudinally extending direction of the handpiece 12 and has teeth 58 formed on both side edges thereof. Blade 54 also has a rounded toothed segment 59 formed on the forward end thereof, which toothed segment 59 extends around and continuously connects with the toothed edges 58.

The arcuate toothed segment 59 performs the cutting which occurs during a bone cutting operation. This portion of the blade, such as is illustrated by the point T in FIG. 1, undergoes a movement which defines a substantially closed noncircular loop 61 as illustrated in FIG. 5, which loop is elongated and is similar to an ellipse. This path of movement has a portion 62 which effectively comprises the cutting stroke, whereas the opposite portion 63 effectively comprises the return stroke of the blade. However, due to the arcuate portion 64 which exists near the end of the cutting stroke 62, this permits the blade to be effectively moved longitudinally along a bone to form an elongated cut therein.

OPERATION

The operation of the surgical saw according to the present invention will be briefly described to insure a complete understanding thereof.

When it is desired to utilize the saw, the shank 57 of the blade 14 is inserted between the section 47 and the projection 48. The lever 56 is then manually turned to tighten the screw 54, thereby causing the shank 57 to be tightly clamped between the section 47 and the projection 48.

With the saw in condition for operation, power is then supplied to the handpiece 12 from an external power source, such as an electric motor and a flexible drive cable (not shown), which cable is connected to the input shaft 21 so as to rotatably drive same. The input shaft 21, through the gear 24, causes rotation of the driven shaft 29 and of the eccentric 33 fixed thereon. This in turn causes the rearward end of the blade holding member 36 to move in a circular path about the axis of the shaft 29, which circular path has a radius R equal to the eccentricity of the eccentric 33.

The rotation of shaft 29 also causes a corresponding rotation of gear 37, whih in turn rotates gear 38 and shaft 39. Since gears 37 and 38 are of equal diameter in the illustrated embodiment, shaft 39 is rotated at the same rate as the shaft 29 but in the opposite rotational direction. This thus causes rotation of the eccentric 42 which is confined within the slot 43. Since slot 43 is elongated in the longitudinal direction of the blade holding member 36, the rotation of eccentric 42 does not cause or effect the reciprocating movement of the blade holding member 36 in the longitudinal direction thereof. However, the eccentric 42 does function as a pivot for the blade holding member 36, with the blade holding member 36 pivoting around the axis of the eccentric 42. The axis of the eccentric 42 also moves through a circular path of movement as defined by the eccentricity R' of the eccentric, so that the blade holding member 36 and the blade 14 mounted thereon thus undergo a pivotal movement about an axis (as defined by the eccentric 42) which continually shifts both laterally and longitudinally during the driving of the member 36 by the eccentric 33.

Due to the presence of the eccentric 42 and its functioning as a pivot for the blade holding member 36, the rotation of the driving eccentric 33 causes the blade holding member 36 and the blade 14 mounted thereon to angularly pivot about the axis of the eccentric 42, which pivoting of the blade holding member is accompanied by a simultaneous reciprocation of the blade holding member in the longitudinal direction thereof as also caused by the rotation of the eccentric 33. This combination of movements thus causes the tip T of the blade 14 to move through an endless path which resembles the loop 61 as illustrated in FIG. 5.

When the saw 11 is used for cutting a bone, the saw is positioned so that the arcuate toothed sector 59 extends substantially in the longitudinal direction of the bone. Upon energization of the driving mechanism, whereupon the blade 14 is moved through a path of motion similar to the path 61 illustrated in FIG. 5, the arcuate toothed portion 59 penetrated the bone, which penetration occurs primarily during the cutting stroke 62. When it is desired to lengthen the cut within the bone, the saw can be moved laterally in the longitudinal direction of the bone whereupon cutting occurs along the arcuate portion 64 of the working stroke so as to lengthen the cut.

The exact configuration of the path 61 and the relative magnitude of the cutting stroke and the retraction stroke, as respectively measured in the vertical and horizontal directions in FIG. 5, can be adjusted by varying the magnitude of the eccentricity R and/or R'. The variation in these eccentricities can be accomplished by replacing the existing shaft 29 and/or 39 and replacing same by a shaft having a different eccentric thereon. If desired, the eccentric as provided on the shaft could be adjustable by utilizing conventional techniques. The variation in the magnitude of the eccentrics will result in the path 61 having a different configuration. For example, by varying the magnitude of the eccentricity R associated with the driving eccentric 33, this will result in a corresponding variation in the linear reciprocation of the saw blade, which linear reciprocation is represented by the horizontal width of the loop 61 illustrated in FIG. 5. On the other hand, when it is desired to vary the length of the working stroke 62, which working stroke is diagrammatically illustrated as extending vertically in FIG. 5, then this can be accomplished by varying the magnitude of the differential E between the eccentrics. Variation in the magnitude of E can obviously be accomplished by varying either or both R and R'.

MODIFICATION

FIGS. 7 and 8 illustrate therein a modified embodiment of the present invention which utilizes much of the structure incorporated in the embodiment of FIGS. 1–4. Accordingly, the embodiment of FIGS. 7 and 8 has been identified by the same reference numerals used to designate the corresponding parts of FIGS. 1–4 except that the numerals in FIGS. 7 and 8 have been additionally distinguished by the addition of a prime (') thereto.

In the embodiment of FIGS. 7 and 8, the handpiece 12' again includes an elongated tubular housing 16' having an opening extending therethrough, which opening contains therein a driving mechanism which possesses a rotatable eccentric 33' drivingly connected to the rearward end of an elongated blade holding member 36'. The eccentric 33 in this embodiment is surrounded by a conventional antifriction bearing 71. The rotation of eccentric 33' again causes the rearward end of the blade holding member 36' to be moved in a circular path identical to the effect caused by the eccentric 33 in FIGS. 1–4.

However, the embodiment of FIGS. 7 and 8 utilizes a modified pivot structure 40' which includes a cylindrical support or pivot member 73 which is disposed adjacent the forward end of the housing 16' and is pivotally supported within a recess 74 formed therein. The cylindrical support member 73 has cylindrical projections 76 of reduced diameter projecting outwardly from the opposite ends thereof, which projections 76 are in turn pivotally supported within small recesses formed in the housing. The housing thus supports the member 73 for pivotal displacement about its longitudinal axis, which axis extends substantially perpendicular to the elongated opening which is formed in the housing.

The support member 73 has a cylindrical bore 72 extending transversely therethrough, and an intermediate portion of the blade holding member 36 extends through the opening 72 whereby the blade holding member 36 is slidably supported on the pivot member 73 and extends substantially perpendicular to the pivot axis thereof.

The operation of the structure in FIGS. 7 and 8 is substantially the same as the operation described above relative to FIGS. 1–4. That is, when the eccentric 33' is rotatably displaced, it causes a corresponding circular displacement of the rearward end of the blade holding member 36', which causes the blade holding member 36' to be angularly pivoted about the pivot axis defined by the support member 73, while at the same time the blade holding member 36 is linearly displaced in a reciprocating manner due to same being slidably supported in the opening 72. This thus results in the outermost end or tip of the blade being moved through a path 77 havng a configuration similar to that illustrated in FIG. 6, which path 77 again comprises an endless substantially elliptical loop having a working or cutting stroke 78 on one side thereof and a return stroke 79 on the opposite side thereof. As illustrated in FIG. 6, the intermediate pivot structure 40' possessing a fixed pivot axis (in contrast to a movable pivot axis as in the embodiment of FIGS. 1–4) results in the path 77 having an increased stroke (as measured vertically in FIG. 6) in contrast to the retraction stroke (as measured horizontally in FIG. 6).

In the embodiment of FIGS. 7 and 8, the cutting stroke associated with the movement path of the blade can again be selectively varied by replacing the eccentric 33' with a new eccentric having the desired magnitude of eccentricity. Alternately, the eccentric 33' could be adjustable if desired.

FIGS. 9 and 10 illustrate therein a further embodiment of the present invention which is similar to the embodiment of FIGS. 1–4, and accordingly FIGS. 9 and 10 have been identified by the same reference numerals used to designate corresponding parts of FIGS. 1–4 except for the addition of a double prime ('') thereto.

The embodiment of FIGS. 9 and 10 is structurally identical to the embodiment of FIGS. 1–4 except that there is additionally provided a rotatable idler gear 81 disposed between and in meshing engagement with the gears 37'' and 38''. The idler gear 81 is supported in a manner similar to the gear 38'' in that it is non-rotatably keyed to a stub shaft 82 which is supported on the housing 16'' by antifriction bearings 83. The gear 81 functions solely as an idler gear so that the gears 37'' and 38'', and the eccentrics 33'' and 42'' associated therewith, respectively, thus rotate in the same direction. This is in contrast to the embodiment of FIGS. 1–4 wherein the gears 37 and 38 and the respective eccentrics rotate in opposite directions.

The eccentric 42'' is preferably eccentrically displaced from the rotational axis of the gear 38'' by a distance which is substantially less than the eccentricity between the eccentric 33'' and the gear 37'', thereby providing for the desired elliptical path of movement of the free end of the cutting blade. For example, the eccentricity of eccentric 33'' may be approximately 3/16 inch, whereas the eccentricity of eccentric 42'' may be approximately 1/16 inch.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an inclusive property or privilege is claimed are defined as follows:

1. In a surgical cutting device having a housing, an elongated blade holding member movably supported relative to said housing, said blade holding member being adapted to have a cutting blade mounted on the outer end thereof, and drive means mounted on said housing and interconnected to said blade holding member for moving same, comprising the improvement wherein:

said drive means includes crank means rotatable about an axis and connected to said blade holding member adjacent the inner end thereof for causing the inner end of said blade holding member to be movably displaced in a circular pattern within a plane which is substantially perpendicular to the rotational axis of said crank means, said crank means including a drive crank member which is rotatable about and eccentrically displaced relative to said rotational axis, said crank member being disposed directly in engagement with said blade holding member adjacent the inner end thereof; and support means pivotally and linearly slidably supporting said blade holding member on said housing for permitting simultaneous angular oscillation and linear reciprocation of said blade holding member within a plane substantially perpendicular to said rotational axis in response to rotation of said crank means, said support means engaging said elongated blade holding member intermediate the ends thereof so as to be disposed between the rotatable crank means and the blade, said support means including a support member mounted on said housing for angular movement about a support axis which is fixed relative to said housing, said support member comprising a support crank member which is rotatable about and eccentrically displaced relative to said support axis, said support axis being substantially parallel to but spaced from said rotational axis, one of said support and crank members having slot means associated therewith and extending in the elongated direction of said blade holding member for slidably supporting said blade holding member for linear movement in a direction which is parallel to the longitudinal direction of said blade holding member and perpendicular to said support axis; and driving means drivingly interconnecting the drive crank member and the support crank member for simultaneous rotation, whereby the cutting edge of the blade is cyclically moved through a path which defines a closed endless loop in response to movement of said blade holding member by said crank means.

2. A device according to claim 1, wherein the eccentricity of the drive crank member relative to said rotational axis is greater than the eccentricity of said support crank member relative to said support axis.

3. A device according to claim 1, wherein said driving means causes rotation of said drive and support crank members at substantially the same rotational speed but in opposite rotational direction.

4. A device according to claim 1, wherein said slot means comprises an elongated slot formed within and extending longitudinally of said blade holding member, and said support crank member being engaged within said slot.

5. A device according to claim 1, wherein the driving means for causing simultaneous rotation of the support and drive crank members includes gear means drivingly connected therebetween.

6. In a surgical cutting device having a housing, an elongated blade holding member movably supported on said housing, said blade holding member being adapted to have a cutting blade releasably attached to the outer end thereof, the improvement comprising drive means drivingly coacting with the blade holding member for causing the cutting edge of said blade to be cyclically moved through a path which defines a closed noncircular endless loop, said drive means including first eccentric means rotatable about a first axis which is substantially perpendicular to the plane defined by said loop, said first eccentric means being drivingly engaged with a portion of said blade holding member for causing circular displacement thereof in a plane which is substantially perpendicular to said first axis, said drive means including second eccentric means rotatable about a second axis which is spaced from but substantially parallel to said first axis, said second eccentric means being drivingly engaged with a part of said blade holding member for causing movement of said part within said plane in a direction substantially transverse to the longitudinally extending direction of said blade holding member, relative movement permitting means coacting between said second eccentric means and said blade holding member for permitting relative slidable movement therebetween substantially in the longitudinal direction of said blade holding member, said relative movement permitting means preventing relative movement between the blade holding member and said second eccentric means in said transverse direction so that said part of the blade holding member is moved in said transverse direction in response to rotation of said second eccentric means, and means drivingly interconnecting said first and second eccentric means for simultaneous rotation about their respective axes.

7. A device according to claim 6, wherein said first eccentric means includes a first substantially cylindrical crank member which is eccentrically displaced relative to and rotatable about said first axis, said portion of said holding member having cylindrical opening means therein in which is accommodated said first crank member whereby said portion is displaced along a circular path in response to rotation of said first crank member, said second eccentric means including a second cylindrical crank member which is eccentrically displaced relative to and rotatable about said second axis, said relative movement permitting means including an elongated slot formed in and extending longitudinally of said blade holding member, said second crank member being engaged within said slot so that said crank member can be slidably displaced in the elongted direction of said slot.

8. A device according to claim 7, wherein said first and second axes intersect the elongated blade holding member at locations which are spaced from one another in the longitudinally extending direction of the blade holding member.

9. A device according to claim 8, wherein the eccentricity of one of said crank members relative to its axis is greater than the eccentricity of the other crank member relative to its respective axis.

10. A device according to claim 7, wherein the means causing simultaneous rotation of the first and second eccentric means causes said first and second eccentric means to be rotated the same number of rotations per unit time.

* * * * *

UNITED STATES PATENT OFFICE
CERTIFICATE OF CORRECTION

Patent No. 3,978,862   Dated September 7, 1976

Inventor(s) Marshal Morrison

It is certified that error appears in the above-identified patent and that said Letters Patent are hereby corrected as shown below:

Line [75]   Address of inventor should read:

Township of Comstock,
   County of Kalamazoo, Michigan.

Line [73]   Address of Assignee should read:

Kalamazoo, Michigan.

Signed and Sealed this

Seventh Day of December 1976

[SEAL]

Attest:

RUTH C. MASON
Attesting Officer

C. MARSHALL DANN
Commissioner of Patents and Trademarks